United States Patent [19]

Simpson

[11] 3,985,558

[45] Oct. 12, 1976

[54] DENTAL ALLOY AND AMALGAM

[75] Inventor: Harold H. Simpson, Fraser, Mich.

[73] Assignee: Sybron Corporation, Rochester, N.Y.

[22] Filed: Mar. 28, 1975

[21] Appl. No.: 563,248

[52] U.S. Cl. ............................ 75/169; 75/134 N; 75/134 B; 75/134 C
[51] Int. Cl.² ...................... C22C 7/00; C22C 30/00
[58] Field of Search .......... 75/173 C, 134 C, 134 B, 75/169, 154, 175 R

[56] References Cited
UNITED STATES PATENTS

| | | | |
|---|---|---|---|
| 2,281,991 | 5/1942 | Poetschke | 75/173 C |
| 3,871,876 | 3/1975 | Asgar et al. | 75/169 |

Primary Examiner—L. Dewayne Rutledge
Assistant Examiner—E. L. Weise
Attorney, Agent, or Firm—Theodore B. Roessel; Owen D. Marjama

[57] ABSTRACT

A dental amalgam which comprises about 40 to 50 weight percent mercury and about 50 to 60 weight percent of an alloy which comprises 24 to 45 weight percent silver, 28 to 42 weight percent copper and 29 to 34 weight percent tin, and where the atomic percentage of the total amount of silver plus copper is about 3 times greater than the atomic percentage of tin.

7 Claims, No Drawings

DENTAL ALLOY AND AMALGAM

BACKGROUND OF THE INVENTION

This invention relates in general to a dental composition and more specifically to a novel dental alloy and dental amalgam suitable for use in repairing carious tooth structure.

Dental amalgams made by triturating a silver-tin-copper alloy with mercury to form a coherent plastic mass that is settable in a few minutes has been in use since before the turn of the century. In the midst of today's rapidly advancing technology in the health care fields, the use of dental amalgam remains the technique of choice by the dental profession in repairing carious tooth structure.

Conventional dental amalgam alloys are comprised basically of a silver-tin alloy compound containing about 74% by weight silver and 26% by weight tin, with smaller amounts of copper and zinc, optionally replacing silver and tin. This alloy when amalgamated is not completely suitable because of deficiencies with regard to strength properties, reisitance to corrosion and static flow and creep.

The advent of gas atomized spherical particle amalgam alloys brought about substantial improvement in the strength of dental amalgams, but deficiencies still remained with respect to the resistance to corrosion, static flow and creep of these alloys.

The available dental alloys that demonstrate the greatest resistance to corrosion and static creep are an admixture of of two alloys. The major alloy comprises the conventional chemistry described above, and the minor alloy comprises silver with a high concentration of copper and little or no tin. These admixed alloys exhibit good resistance to corrosion and static creep, but are deficient in other physical and mechanical properties, and demonstrate broad variances in physical and mechancial properties and handling characteristics from production batch to production batch. In general most of the aforementioned alloys have a silver content of about 70% by weight or greater, and are therefore high cost alloys due to the high concentration of the silver which is also the most expensive element comprising the alloy.

Although the dental amalgam alloys described above have been satisfactory for use in repairing carious tooth structure, it can be seen from a discussion of some of their limitations, that there has been a continuing need in the dental profession for improved amalgam formulations which will improve on existing materials.

OBJECTS OF THE INVENTION

It is therefore an object of this invention to provide an improved dental alloy suitable for amalgamation with mercury which exhibits outstanding physical and mechanical properties and handling characteristics.

It is another object of this invention to provide a dental amalgam which exhibits outstanding physical and mechanical properties and handling characteristics.

SUMMARY OF THE INVENTION

The foregoing objects and others are accomplished in accordance with this invention by providing a new and novel dental alloy which is amalgamatable by trituration with mercury. The alloy comprises silver in a concentration of about 24 to 45 weight percent; copper in the concentration of about 28 to 42 weight percent; and tin in a concentration of about 29 to 34 weight percent. A particularly preferred composition which exhibits outstanding physical, mechanical and handling characteristics comprises about 40 weight percent silver, 30 weight percent copper and 30 weight percent tin.

It has been found that within the concentration ranges set forth above, that a critical relationship in atomic percentage exists between the total atomic percentage of silver and copper to the atomic percentage of tin. Although the theory or mechanism for this effect is not fully understood, it has been found that in order to assure superior physical, mechanical and handling properties for the alloy of the present invention, the atomic percentage of tin must be maintained within a narrow concentration of about 24 to 25 atomic percent of the total atomic percentage of the silver, copper and tin. Stated another way, the atomic ratio of silver plus copper to the tin must be about 3 to 1.

Optionally the silver and/or copper may be replaced with up to about 2 weight percent zinc. In this case, the atomic ratio of silver, copper and zinc to the tin should also be maintained at about 3 to 1.

The alloy described above is amalgamated by trituration with mercury in a concentration of about 40 to 50 weight percent mercury with the balance of the amalgam comprising the alloy.

DESCRIPTION OF THE PREFERRED EMBODIMENTS

The following examples further specifically define the present invention with respect to a method of making and testing a silver-tin-copper dental alloy and an amalgam using the alloy. The percentages in the disclosure, examples and claims are by weight unless otherwise indicated. The Examples below are intended to illustrate various preferred embodiments of the present invention.

EXAMPLE I

A dental alloy comprising 37.70 weight percent silver (31.85 At%), 31.80 weight percent tin (24.41 At.%) and 30.50 weight percent copper (43.74 At.%) is prepared by first forming a molten alloy in the above concentration ranges and atomizing said alloy at approximately 2,000° F. Atomization is achieved in a conventional manner as described in U.S. Pat. No. 3,305,356 at column 2, lines 9–50 which is incorporated herein by reference. The alloy is then collected and classified in a 325 mesh sieve. The fraction passing through the sieve is retained as the dental alloy product.

EXAMPLE II

A second alloy comprising 39.90 weight percent silver (34.04 At.%), 31.30 weight percent tin (24.26 At.%) and 28.80 weight percent copper (41.70 At.%) is prepared using the techniques set forth in Example I above.

EXAMPLE III

A third alloy comprising 24.00 weight percent silver (19.02 At%), 34.00 weight percent tin (24.49 At.%) and 42.00 weight percent copper (56.49 At.%) is prepared by the method set forth above in Example II.

In order to improve the physical and mechanical properties and handling characteristics of the alloys formed in Examples I, II, and III above, these alloys were annealed in a vacuum at a temperature between about 150° C and 180° C for three to four hours.

Alternatively, the vacuum may be replaced with an inert atmosphere such as argon, if desired. If a vacuum or inert atmosphere is not used it may become necessary to acid etch the alloy in order to remove undesirable surface oxides.

EXAMPLE IV

Amalgam test specimens using the alloys formed in Examples I, II, and III above are prepared as follows:

A test specimen using the alloy described above is prepared by triturating 45 weight percent mercury with 55 weight percent of the particular alloy in a mulling cup on a Kerr/McShirley mechanical mixer which is operated for approximately ten seconds. Typically, six to eight minutes work time before set with 45 weight percent mercury is desired. The resulting coherent plastic mass of unset triturated amalgam is then placed in an ADA standard mold cavity and condensed by applying a static load of 2030 psi for 55 seconds. The load is then removed and the specimen is immediately ejected from the mold. The specimen is then stored at 37° C until the start of the test procedure. The exact procedural details of testing can be determined with reference to American Dental Association Specification No. 1 for Alloy for Dental Amalgam with June 1970 revision (See Guide to Dental Material and Devices — 6th Ed. American Dental Association publication, 211 E. Chicago Ave., Chicago, Ill., 60611, pp. 168–171).

Tensile strength measurements are taken at 15 minutes, flow at 3 to 24 hours, and dimensional changes measured at 5 minutes to 24 hours according to the ADA specifications described above. The results of these tests are tabulated below in Table I.

TABLE I

| Tensile Strength psi crosshead speed 0.02 in/min. | | | | |
|---|---|---|---|---|
| | ADA std | Example 1 | Example 2 | Example 3 |
| 15 min | 290 | 839 | 935 | 993 |
| 24 hours | — | 8,147 | 8,136 | 5,093 |
| Compressive Strength psi crosshead speed 0.01 in/min | | | | |
| 1 hour | 11,600* | 32,823 | 43,553 | 42,441 |
| 24 hours | — | 83,298 | 82,914 | 53,821 |
| Dimensional change percent | | | | |
| | ±0.2 | −0.071 | −0.06 | −0.038 |
| Flow percent | | | | |
| | 3.0 | 0.095 | 0.094 | 0.088 |
| Creep percent | | | | |
| | 5.0* | 0.035 | 0.032 | 0.046 |
| Corrosion Resistance | | | | |
| | | good | good | good |

*Proposed

It can be seen from the data contained in Table I that the amalgams employing the alloy of the present invention exhibit properties which exceed ADA standards. In addition, these amalgams exhibit outstanding handling characteristics with respect to work time, condensing, carving, marginal adaptation and polish. When deviating from the compositional range and atomic ratio set forth above, a significant deterioration occurs in the handling characteristics of the alloy.

Other modifications and ramifications of the present invention would appear to those skilled in the art upon reading this disclosure. These are also intended to be within the scope of this invention.

I claim:

1. A dental alloy which consists essentially of about 24 to 45 weight percent silver, 28 to 42 weight percent copper and 29 to 34 weight percent tin, and where the atomic percentage of the total amount of silver plus copper is about 3 times greater than the atomic percentage of tin.

2. The alloy of claim 1 which zinc replaces silver and/or copper up to a maximum of 2 percent by weight.

3. A dental composition amalgamatable by trituration with mercury which consists essentially of about 40 weight percent silver, 29 weight percent copper and 31 weight percent tin.

4. A dental amalgam which consists essentially of about 40 to 50 weight percent mercury and about 50 to 60 weight percent of an alloy which comprises 24 to 45 weight percent silver, 28 to 42 weight percent copper and 29 to 34 weight percent tin, and where the atomic percentage of the total amount of silver plus copper is about 3 times greater than the atomic percentage of tin.

5. The amalgam of claim 4 in which the alloy consists essentially of about 40 weight percent silver, 29 weight percent copper and 31 weight percent tin.

6. A dental alloy which consists essentially of about 24 to 45 weight percent silver, 28 to 42 weight percent copper and 29 to 34 weight percent tin, and where the atomic percentage of the total amount of silver plus copper is about 75 to 76 percent and the atomic percentage of tin is from about 24 to 25 percent.

7. A dental amalgam which consists essentially of about 40 to 50 weight percent mercury and about 50 to 60 weight percent of an alloy which comprises 24 to 45 weight percent silver, 28 to 42 weight percent copper and 29 to 34 weight percent tin, and where the atomic percentage of the total amount of silver plus copper is about 75 to 76 percent and the atomic percentage of tin is from about 24 to 25 percent.

* * * * *